(12) United States Patent
Nemeh et al.

(10) Patent No.: US 8,660,669 B2
(45) Date of Patent: Feb. 25, 2014

(54) CONCURRENT TREATMENT OF ORAL MALADIES USING DIRECT CURRENT ELECTRICITY

(75) Inventors: Issam Nemeh, Westlake, OH (US); George Nicholas Szatkowski, Charlottesville, VA (US)

(73) Assignee: Biolectrics LLC, Cleveland, OH (US)

( * ) Notice: Subject to any disclaimer, the term of this patent is extended or adjusted under 35 U.S.C. 154(b) by 1079 days.

(21) Appl. No.: 12/205,062

(22) Filed: Sep. 5, 2008

(65) Prior Publication Data

US 2009/0117513 A1    May 7, 2009

Related U.S. Application Data

(63) Continuation-in-part of application No. 11/850,661, filed on Sep. 5, 2007, now abandoned.

(51) Int. Cl.
*A61N 1/20* (2006.01)
(52) U.S. Cl.
USPC .......................................... 607/134; 433/216
(58) Field of Classification Search
USPC .................................. 433/215, 216; 607/134
See application file for complete search history.

(56) References Cited

U.S. PATENT DOCUMENTS

| | | | |
|---|---|---|---|
| 1,389,662 A | 9/1921 | Irwin | |
| 2,151,738 A | 3/1939 | Buhse | |
| 3,118,450 A | 1/1964 | Freeman et al. | |
| 3,207,161 A | 9/1965 | Dietz | |
| 3,215,139 A | 11/1965 | Dietz | |
| 3,380,446 A | 4/1968 | Martin | |
| 3,502,076 A | 3/1970 | Bertolini | |
| 4,153,060 A * | 5/1979 | Korostoff et al. | 607/51 |
| 4,175,565 A | 11/1979 | Chiarenza et al. | |
| 4,244,373 A * | 1/1981 | Nachman | 607/9 |
| 4,509,519 A | 4/1985 | Detsch | |
| 4,924,880 A | 5/1990 | O'Neill et al. | |
| 5,207,231 A | 5/1993 | Fakhri | |
| 5,372,501 A | 12/1994 | Shalvi | |
| 5,433,735 A | 7/1995 | Zanakis et al. | |
| 5,490,520 A | 2/1996 | Schaefer et al. | |
| 5,496,256 A | 3/1996 | Bock et al. | |

(Continued)

FOREIGN PATENT DOCUMENTS

WO    2005062710    7/2005

OTHER PUBLICATIONS

Tronstad et al., "Effect of Electric Current and Silver Electrodes on Oral Bacteria", Endod Dent Traumatol 1985; 1:112-115.

(Continued)

*Primary Examiner* — Christopher D Koharski
*Assistant Examiner* — Frances Oropeza
(74) *Attorney, Agent, or Firm* — Ryan Kromholz & Manion, S.C.

(57) ABSTRACT

A method and apparatus for the concurrent treatment of multiple oral diseases and defects while promoting general oral hygiene utilizing direct current electricity. Electrodes are used to deliver a direct current to the gingival tissues of a mouth in order to achieve a number of therapeutic, prophylactic, and regenerative benefits. These benefits include killing oral microbes, increasing oral vasodilation, improving oral blood circulation, reversing oral bone resorption, promoting oral osteogenesis, treating gum recession, and fostering gingival regeneration. Other benefits include the treatment of gingivitis, perdiodontitis, and oral malodor while also promoting general oral hygiene.

15 Claims, 4 Drawing Sheets

(56) References Cited

U.S. PATENT DOCUMENTS

| | | | |
|---|---|---|---|
| 5,725,377 | A | 3/1998 | Lemler et al. |
| 5,741,500 | A | 4/1998 | Yates |
| 5,792,067 | A | 8/1998 | Karell |
| 6,212,435 | B1 | 4/2001 | Lattner et al. |
| 6,212,535 | B1 | 4/2001 | Weikart et al. |
| 6,254,391 | B1 | 7/2001 | Darnell |
| 6,265,391 | B1 | 7/2001 | Herbert |
| 7,044,737 | B2 | 5/2006 | Fu |
| 7,118,377 | B2 | 10/2006 | Inoue et al. |
| 7,163,399 | B2 | 1/2007 | Kajimoto et al. |
| 7,775,795 | B2 | 8/2010 | Khawaled et al. |
| 7,874,294 | B2 | 1/2011 | Burger |
| 7,917,223 | B2 | 3/2011 | Madjar et al. |
| 8,060,220 | B2 | 11/2011 | Liebergesell et al. |
| 2006/0271148 | A1 | 11/2006 | Liebergesell et al. |
| 2007/0203389 | A1* | 8/2007 | Bergman ........................ 600/13 |
| 2007/0224572 | A1 | 9/2007 | Jon |
| 2007/0259316 | A1 | 11/2007 | Conrad et al. |
| 2008/0003540 | A1* | 1/2008 | Khawaled et al. ............ 433/215 |
| 2008/0233541 | A1* | 9/2008 | De Vreese et al. ............ 433/216 |
| 2008/0280248 | A1 | 11/2008 | Pitts |
| 2009/0117513 | A1 | 5/2009 | Nemeh |
| 2012/0156648 | A1 | 6/2012 | Kaufman |

OTHER PUBLICATIONS

Kalinowski et al., "Low-Voltage Direct Current as a Fungicidal Agent for Treating Onychomycosis", Journal of the Am. Pod. Med. Assoc. vol. 94, No. 6, Nov./Dec. 2004; pp. 565-572.

Matsunaga, T. et al., Electrode System for the Determination of Microbial Populations, Applied and Environmental Microbiology, vol. 37 No. 1, Jan. 1979, p. 117-121.

Caubet, R., et al., A Radio Frequency Electric Current Enhances Antibiotic Efficacy . . . , Antimicrobial Agents and Chemotherapy. vol. 48, No. 12, Dec. 2004, pp. 4662-4664.

Giladi, M., et al., Microbial Growth Inhibition by Alternating Electric Fields, Antimicrobial Agents and Chemotherapy, vol. 52, No. 10, Oct. 2008, pp. 3517-3522.

Del Pozo, J.L., et al., The Electricidal Effect is Active in an Experimental Model . . . , Antimicrobial Agents and Chemotherapy. vol. 53, No. 10, Oct. 2009, pp. 4064-4068.

Dei Pozo, J.L., et al., Effect of Electrical Current on the Activities of Antimicrobial Agents . . . Antimicrobial Agents and Chemotherapy. vol. 53, No. 1, Jan. 2009, pp. 35-40.

Del Pozo, J.L., et al., The Electricidal Effect: Reduction of *Staphylococcus* . . . , Antimicrobial Agents and Chemotherapy, vol. 53, No. 1, Jan. 2009, pp. 41-45.

Davidovitch, Z., et. al., Effect of electric currents on gingival cyclic nucleotides in vivo (Abstract). Journal of Periodontal Research, 1980, 15: 353-362.

Hashimoto, H., Effect of micro-pulsed electricity on experimental tooth movement (Abstract). Nihon Kyosei Shika Gakkai Zasshi, Aug. 1990, 49(4):352-61.

Horning, GM., et al., The prevalence of periodontitis in a military treatment problem (Abstract). J Am Dent Assoc., Nov. 1990, 121(5):616-22.

Onkormanyzat, F., et al., The use of iontophoresis in dental practice (Abstract). Fogorv Sz. Jun. 1993, 86(6):205-12.

Wang, Q., et al., Osteogenesis of electrically stimulated bone cells mediated in part by calcium ions (Abstract), Clin Orthop Relat Res. Mar. 1998, (348):259-68.

Davidovitch, Z, et al., Electric currents, bone remodeling, and orthodontic tooth movement. II. Increase in rate of tooth . . . (Abstract), Am J Orthod, Jan. 1980, 77(1):33-47.

Hashimoto, H., Effect of micro-pulsed electricity on experimental tooth movement (Abstract). Nihon Kyosei Shika Gakkai Zasshi, Aug. 1990, 48(4):352-61.

Buch, F., et al., Direct current influence on bone formation in titanium implants (Abstract). Biomateriais, Nov. 1984, 5(6):341-6.

Puhar, I., et al., Efficacy of electrical neuromuscular stimulation in the treatment of chronic periodontitis. J Periondontal Implant Sci 2011; 41:117-122.

Bolton. L., et al., Direct-Current Bactericidal Effect on Intact Skin. Antimicrobial Agents and Chemotherapy, Jul. 1980, vol. 18, No. 1, pp. 137-141.

Ehrlich, G.D., et al., Engineering Approaches for the Detection and Control of Orthopaedic Biofilm Infections, Clin Orthop Relat Res. Aug. 2005, (437):59-66.

Matl, FD., et al., Augmentation of antibiotic activity by low-frequency electric . . . (Abstract). Bioelectromagnetics, Jul. 2011, 32(5):367-77.

Sandhi, SP., et al., Comparative evaluation of different strengths of electrical current . . . (Abstract). Indian J Dent Res. Apr.-Jun. 2010; 21(2):207-12.

Kaynak, D., et al., A histopathologic investigation on the effects of electrical stimulation . . . (Abstract). J Periodontol, Dec. 2005, 76(12):2194-204.

Hagiwara, T., et al., Effect of electrical stimulation on mandibular distraction osteogenesis (Abstract). J Craniomaxillofac Surg, Feb. 2000, 28(1):12-9.

Chakkalakai, DA., et al., Electrophysiology of direct current stimulation of fracture . . . (Abstract). IEEE Trans Biomed Eng., Nov. 1990, 37(11):1048-58.

Kane, WJ. Direct current electrical bone growth stimulation for spinal fusion (Abstract). Spine (Phila Pa 1976), Mar. 1988, 13(3):363-5.

Periodontal Disease Fact Sheet, American Academy of Periodontology, www.perio.org/newsroom/periodontal-disease-fact-sheet, Oct. 10, 2013.

manuelderegil@xxxxxxxxx. "Perioprotect ripoff", perioprotect. ripoff, Mar. 20, 2009.

Petersen, P.E., et al., Strengthening the prevention of periodontal disease: the WHO approach, J Periodontol, Dec. 2005, vol. 76, No. 12, pp. 2187-2193.

Pitman, S., US Army develops tooth-cleaning gum, Cosmetics design.com, Dec. 21, 2005.

Bloomberg Businessweek, Why P&G's Smile is So Bright, Jul. 31, 2002, 4 pages.

Hitti, M., 9 Risk Factors for Tooth Loss, WebMD.com, Nov. 11, 2005, 3 pages.

American Dental Association, Key Dental Facts, Sep. 2008, 26 pages.

Karolefski, J., Changing Habits. Supermarket News., Feb. 16, 2009, http://supermarketnews.com/print/nonfood/changing-habits, 4 pages.

Dental Managment: Cost of Deep Perio Cleaning from a Dentist . . . Oct. 10, 2013, http://thewealthydentist.com/SurveyResults/119-Perio-Cleaning.htm, 2 pages.

Johnsen. M., 2009 Hot Products: Editor's Picks. Drug Store News, Jun. 2009, www.drugstorenews.com, 17 pages.

Ichimura. K., et al., Effect of weak electric current on reducing oral bacteria in vitro. Bull. Tokyo dent. Coll., vol. 42, No. 2, pp. 97-100, May 2001.

Poortinga, A.T., et al., Electric field induced desorption of bacteria from a conditioning film covered substratum. Biotechnology and Bioengineering, vol. 76(4):395-99 Dec. 2001.

Glazer, P.A., et al., Electricity: The history and science of bone growth stimulation for spinal fusion. The Orthopaedic Journal at Harvard Medical School, 2002, pp. 63-67.

Albandar, J.M., et al., Gingival recession, gingival bleeding, and dental calculus in adults 30 years of age and older . . . J Periodontal, Jan. 1999, vol. 70, No. 1, pp: 30-43.

Banga, A.K., et al., Iontophoresis and eleotroporation: comparisons and contrasts. International Journal of Pharmaceutics 179 (1999) pp. 1-19.

Piekarski, K., et al., Osteogenetic stimulation by externally applied DC current. Acta Orthop. Scand. vol. 49, pp. 113-120, 1978.

Hartshorne, E. On the causes and treatment of pseudarthrosis and especially that form of it sometimes called supernumerary joint. Am J Med, Jan. 1841; vol. 1; pp. 121-156.

* cited by examiner

CONCURRENT TREATMENT OF ORAL MALADIES USING DIRECT CURRENT ELECTRICITY

CROSS-REFERENCE TO RELATED APPLICATIONS

This application is a continuation-in-part of application Ser. No. 11/850,661 filed on Sep. 5, 2007 now abandoned.

BACKGROUND

This invention relates to a method of concurrently promoting general oral hygiene, treating periodontal diseases such as gingivitis, killing oral microbes including cavity-causing bacteria, increasing blood flow in oral tissues, promoting gingival tissue regeneration, fostering osteogenesis in the boney structures of the teeth, mouth and related areas, and treating other periodontal and oral maladies through the non-invasive application of weak direct current electricity to the surfaces in the oral cavity, and it also relates to an apparatus suitable for providing direct current electricity for these therapeutic, prophylactic, and regenerative effects.

The benefits of electrical current for the treatment of gingival inflammations, such as gingivitis, are known within the art. However, prolonged gingivitis leads to the formation of periodontal pockets, gingival recession, and bone resorption. If left untreated, gingivitis may develop into perdiodontitis, a condition that may ultimately result in tooth loss. Even if gingivitis is properly treated and eliminated, recessed gums will still remain even after the inflammation subsides. Methods and devices such as those presented by Nachman in U.S. Pat. No. 4,244,373 of Jan. 13, 1981 and by Detsch in U.S. Pat. No. 4,509,519 of Apr. 9, 1985 and by Liebergesell et al. in U.S. patent application Ser. No. 11/499,033 of Nov. 30, 2006 may treat gingivitis but do not offer any way to reverse gingival recession and regenerate any lost gingival tissue.

Gum recession causes many oral care and oral hygiene problems. The receding gums expose the root of the teeth. The exposed root greatly increases sensitivity to heat, cold, and sweets, which can cause discomfort and even pain. The exposed root is also much more vulnerable to tooth decay, greatly increasing the chances for tooth loss.

The normal treatment for severe gum recession involves a gum graft, a type of periodontal surgery in which gingival tissue is surgically removed from a donor area and grafted upon the area affected by gum recession. These surgeries, however, are invasive, costly to the patient, require anesthesia, and usually require two to four weeks of recovery time. This type of surgery also causes scarring to the gingival area receiving the graft. There is an additional risk that the gum graft surgery may actually increase the rate of gum recession.

Other treatments for gum recession focus on a topical application of a regenerative medication. These methods and devices may be effective in promoting gum growth, but are not effective in killing oral microbes, treating gingivitis, increasing oral circulation or promoting osteogenesis (e.g. Yates, U.S. Pat. No. 5,741,500, Apr. 21, 1998). While the effect of regenerating gingival tissues is desirable to the user, such methods and devices fall well short of an all-in-one oral hygiene device.

There are electrical stimulation methods for inducing regeneration, similar to Zanakis et al., U.S. Pat. No. 5,433,735 of Jul. 15, 1985, which have shown promise for generic tissue regeneration, but have not been specifically implemented for gingival tissues. Once again, however, this method of regeneration also does not address any other oral malady such as gingivitis, perdiodontitis, fungal infections, or poor oral blood flow.

Other methods utilizing alternating current electricity for treating gingivitis and promoting oral hygiene, such as Liebergesell at al., U.S. patent application Ser. No. 11/499,033 of Nov. 30, 2006 may be effective, but still have somewhat in the scope of their applications. Direct current electricity has been studied and is well known to kill common oral bacteria ("Effect of electric current and silver electrodes on oral bacteria", Tronstad et al., Endontontics & Dental Traumatology Vol. 1: 112-115, 1985). Likewise, these alternating current methods are not able to provide the benefits of increased oral blood flow, increased osteogenesis, and gingival regeneration.

Electrical current dental treatment devices (see Nachman, U.S. Pat. No. 4,244,373, Jan. 13, 1981) are known to be effective in promoting osteogenesis and treating perdiodontitis, but do not address gingival regeneration. And while this device may be able to kill the bacteria associated with gingivitis and perdiodontitis, the current levels are too low for this device to be effective in killing other types of oral microbes, including fungi. Additionally, in some embodiments, this device creates a current flow not limited to the gingival region, but instead traveling throughout the body, which may have unknown adverse effects. These embodiments also require the use of a wrist strap electrode and electrolyte solution, which, at the very least, is inconvenient and cumbersome for the user.

Similar to the previous method, Detsch, U.S. Pat. No. 4,509,519 of Apr. 9, 1985 utilizes a direct current for treating oral diseases. However, this method does not address gum regeneration in any way. As with some other treatments, the configuration of this device is inconvenient and possibly uncomfortable for the patient. Electrodes are required to be formed around each tooth whose surrounding gingiva is to be treated, which would likely have to be done by a dental professional. This would be both expensive and time consuming for the patient. Likewise, if a patient were missing a tooth or perhaps many teeth, such an apparatus would not be able to be used to treat those regions of the mouth lacking teeth. Such a treatment is not viable for those who rely on dentures, as is seen with the elderly population. Also, such an apparatus requires the attachment of a metallic plate to one's skin outside the mouth. This is cumbersome, unwieldy, and unsightly for the patient. The external electrode method also does not limit the current flow to the gingival tissues, possibly affecting other areas of the body. Lastly, current levels must be manually set for each tooth area. So for each tooth being treated, a corresponding power source must be adjusted rather than have a single point of control for all the electrodes.

Another problem with the existing direct current oral treatment methods and devices of Nachman, U.S. Pat. No. 4,244,373 of Jan. 13, 1981 and of Detsch, U.S. Pat. No. 4,509,519 of Apr. 9, 1985 is that such methods are not effective at killing oral fungus. Under normal conditions, various fungi such as *Candida* yeasts live in the mouth but are kept in check by the immune system. In certain cases, as with an immune-deficient patient, the immune system is not able to control these normally harmless fungal infections. Patients may then develop oral fungal infections such as candidiasis, more commonly known as thrush. Thrush by itself is harmless, but provides a danger since the *Candida* yeasts can spread throughout the body causing widespread infection. These types of systemic infections can be very serious to patients with weakened immune systems, like those undergoing chemotherapy or those having other immunodeficient conditions such as HIV. Chemotherapy patients have to be especially careful when dealing with oral thrush infections, as their weakened immune system requires excellent oral hygiene to prevent such an outbreak.

Another process used to treat perdiodontitis, tooth demineralization, and oral malodor is based on a concept of heating the teeth (see Darnell, U.S. Pat. No. 6,254,391, Jul. 3, 2001). While this method may be effective in killing some types of oral bacteria and thus treating oral malodor, the patient faces an added risk of potentially damaging each tooth's pulp. Necrosis of the pulp can begin with as little as a 5.5° C. increase in pulpal temperatures, which is a risk with any method that heats the teeth. And while it is possible that such a method can also help with tooth remineralization, this process requires an external source of fluoride, as it is not readily available in saliva. Even though such a method may be able to treat oral malodor and kill bacteria, still it is limited in that it does not utilize any type of electricity to stimulate the oral tissues. This renders such a method ineffective at treating conditions of gingival recession or fungal infections.

Direct current stimulation for promoting osteogenesis is known throughout the art. However, existing methods such as Chiarenza, U.S. Pat. No. 4,175,565 of Nov. 27, 1979, may require surgical implantation of electrodes in order to achieve such results. This is inconvenient, painful, and costly to a patient. Other non-invasive methods using direct current for osteogenesis exist but are designed solely for osteogenesis and are not designed to treat gingivitis, increase blood flow, or regenerate gums (e.g., Korostoff et al., U.S. Pat. No. 4,153,060, May 8, 1979).

Therefore, there is a need in the art for a non-invasive method that treats common oral defects and diseases simultaneously. Specifically, a method to concurrently treat gingivitis and perdiodontitis, to kill oral microbes including bacteria, viruses, and fungi, to increase oral blood flow, to regenerate recessed gums, to catalyze oral osteogenesis, and to promote general oral hygiene is greatly desired. Additionally, such a method would prove greatly effective in reducing tooth decay, preventing tooth loss, preventing cavity formation, and treating oral malodor due to its microbiocidal effects. This desired method would also greatly reduce the invasiveness, cost, complexity, recovery, and risks associated with other dental treatments for these conditions.

SUMMARY OF THE INVENTION

This invention encompasses a method and apparatus that delivers microampere-level direct current electricity to the patient's gingival surfaces. This type of treatment is effective for treating for gingivitis, perdiodontitis, and related conditions, for killing or disabling oral microbes including bacteria, viruses, and fungi, for promoting osteogenesis in the teeth and jaw, for increasing blood flow in oral tissues, and for regenerating gingival tissues.

DETAILED DESCRIPTION

It is known in the art that oral bacteria cannot survive when exposed to low-microampere direct current electricity. This method of killing oral bacteria and treating bacteria-caused conditions such as gingivitis has been demonstrated in Nachman, U.S. Pat. No. 4,244,373 of Jan. 13, 1981 and in Detsch, U.S. Pat. No. 4,509,519 of Apr. 9, 1985. Killing oral bacteria has the added benefit of preventing tooth decay and dental caries, or cavities. Generally, tooth decay is attributed to acid-producing bacteria whose acid causes uncompensated demineralization of the teeth.

While researching the effect of direct current electricity on the mouth, the applicants discovered that by increasing the current level to the approximate range of 50 to 250 microamperes, a direct current electrical treatment was able to deliver new and unexpected therapeutic, prophylactic, and regenerative benefits previously unknown in the art.

Specifically, by utilizing a direct current in the aforementioned range, not only did such a treatment kill bacteria, but it was also found to kill or disable viruses and fungus as well. Studies from the podiatric field have shown that higher current levels than those used in existing oral electrical treatments are necessary to effectively treat fungal infections ("Low-Voltage Direct Current as a Fungicidal Agent for Treating Onychomycosis", Kalinowski, et al., Journal of the American Podiatric Medical Association Vol. 94 No. 6: 565-572, 2004). By applying this knowledge of increased current levels from research outside the art, the applicants were able to add fungicidal and viricidal benefits to a method already known to be bactericidal. The applicants' studies have shown that these microbicidal properties take effect within approximately 5 and 15 minutes of treatment.

In addition, the applicants' clinical research unexpectedly demonstrated that a direct current in the approximate range of 50 to 250 microamperes was able to regenerate gingival tissues, providing a non-surgical treatment alternative for those with recessed gums. While the osteogenic properties of electricity have been known in the art, the connection between nonosseous tissue regeneration and electricity were not well known in the art prior to these experiments. The unique current range associated with the method and apparatus of this invention is one of a few effective methods in the dental field to accomplish effective gingival tissue regeneration in a non-surgical manner.

Thus, this method and corresponding apparatus are able to achieve multiple prophylactic, therapeutic, and regenerative effects whose combination was not previously known or available in the art. Namely, these effects are: promotion of oral osteogenesis, destruction or disabling of oral microbes, gingival tissue regeneration, cavity prevention, increased oral vasodilation and oral blood flow, treatment of common oral conditions such as gingivitis and perdiodontitis, and generally improved oral hygiene.

These effects are accomplished by the delivery of direct current to the gums through a plurality of electrodes in direct contact with the inner and outer gingival surfaces. The electrodes may be fashioned out of any electrically-conductive material, including but not limited to silver, stainless steel, copper, gold, platinum, palladium, aluminum, an alloy thereof, electrically-conductive nanotubes, carbonized rubber, electrically-conductive silicone, or electrically-conductive polymers. The electrodes may be composed of the same or of differing materials. These electrodes fit snuggly against the patient's inner and outer gumlines and make direct contact with each gumline to pass direct current electricity across the teeth and neighboring gingival tissues.

The electrodes on each side of the gumline are of the same polarity. Electrodes on opposite sides of the gumline are of different polarities. This allows the current to flow across the teeth and gums to the electrodes positioned on the transverse gumline to complete the electrical circuit. Put another way, all electrodes on the interior gumline will be completely anodic or completely cathodic. All electrodes on the exterior gumline, transverse the interior gumline, would have the opposite polarity. The polarization of these electrodes may be reversed during treatment or in between treatments.

The upper and lower gumlines each have a set of a plurality of polarized electrodes as previously described. This allows for treatment of both the upper and lower gum and bone structures simultaneously. The upper and lower set of electrodes may be powered by two different adjustable power supplies or by the same adjustable power supply.

Electrical conductors then connect these electrodes to an adjustable power supply. All of the anodic electrodes will connect to the positive pole of the power supply and all of the cathodic electrodes will connect to the negative pole of the power supply. The adjustable power supply is capable of delivering a stable, direct current in the approximate range of 1 to 500 microamperes. The preferred current setting for treatment is in the approximate range of 50 to 250 microamperes.

In order to increase conductivity in the tissues adjacent to the electrodes, an ionic or colloidal liquid or gel may be used as a conductive medium to decrease electrical resistance in the mouth. This medium would be placed along any desired areas of desired electrical contact, such as the teeth, gums, or surrounding oral tissues. Examples of such a medium would include, but not be limited to, colloidal silver gel, liquid colloidal silver, colloidal copper gel, liquid colloidal copper, colloidal gold gel, liquid colloidal gold, saline gel, liquid saline or any combination thereof.

Colloidal silver, in whole or in combination, has great promise not only in increasing electrical current flow, but also in offering additional bactericidal benefits. Colloidal silver, in concentrations as little as five parts per million, is known to be bactericidal by inhibiting a bacterium's production of adenosine triphosphate.

This conductive medium may also contain dietary supplements including, but not limited to, oil of oregano. Oil of oregano is believed to have many health benefits and may also be microbicidal. Such microbicidal properties would be effective in treating common oral infections and diseases as well as aiding in preventative oral care.

This conductive medium may also contain teeth whitening agents. This would allow for the addition of teeth whitening to the list of benefits offered by an embodiment of this invention. A whitening agent that is catalyzed by direct current electricity could be included and may even offer reduced teeth whitening treatment times when compared with nonelectrically-catalyzed whitening agents.

Artificial or natural flavorings may also be added to this conductive medium to offer a more appealing taste to the user, similar to the method of flavoring dental fluoride treatments. This flavoring would mask any unpleasant tastes from the ingredients of the conductive medium or as well as any taste of the mouthpiece or electrodes themselves.

Figure 1:
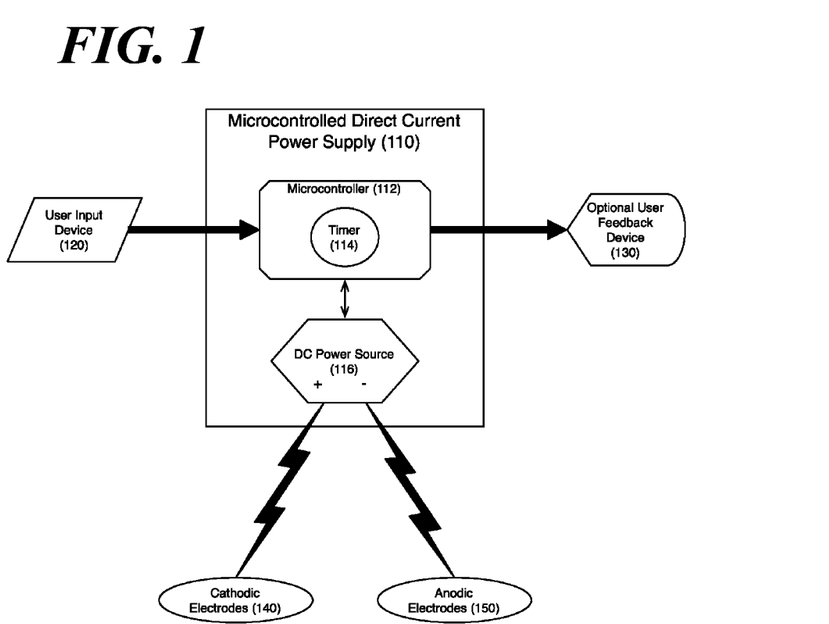
FIG. 1 demonstrates the overall structure of the first embodiment of our invention, including a microcontrolled power source, user input, user feedback and oral electrodes.

FIG. 1 shows one embodiment of a treatment apparatus according to this invention. A user input device 120 is connected to a microcontrolled direct current power supply 110. This input device 120 may include, but not be limited to potentiometer dials, push buttons, switches, toggles, etc. User input device 120 allows the patient to control various aspects of the treatment including but not limited to power on or off, output current levels, treatment program selection, treatment duration, treatment reminders, polarity, etc. Microcontrolled power supply 110 reads the state of input device 120 and adjusts the output current accordingly.

An optional user feedback device 130 is show in FIG. 1 connected to microcontrolled power supply 110. Feedback device 130 may contain various methods and devices capable of relaying treatment information to the user. Feedback device 130 could include, but not be limited to an LCD display, LCD matrix display, color LCD displays, indicator LEDs, LED bar graphs, LED segment displays, OLED displays, audio speakers, vibrating devices, or any combination thereof. Feedback device 130 offers the user information including, but is not limited to, output current level, treatment time elapsed, treatment time remaining, date, time of day, battery power level, treatment reminder indicators or sound alarms, recharging indicators, etc. Feedback device 130 also provides information regarding any state change from input device 120. This allows the user to receive information on how his/her input is affecting the treatment. Feedback device 130 is not required for the operation of this embodiment of the treatment apparatus and may be omitted.

Microcontrolled power supply 110 contains a microcontroller 112 and a direct current power source 116. Microcontroller 112 is electrically connected to input device 120 and is capable of reading the device's state(s). Microcontroller 112, upon reading these state(s), is able to dynamically adjust the output of power source 116. This allows the user to control the level of current generated by the power source 116. Microcontroller 112 is also connected to an optional user feedback device 130. Microcontroller 112 is able to output information related to the treatment duration, current timer status, current levels, and other information to feedback device 130. Microcontroller 112 also has timing capabilities, represented by timer 114, that allow for limiting treatment time based on some predetermined treatment duration. Timer 114 is also used to output the elapsed treatment time to feedback device 130, if present. The user is able to input desired treatment parameters such as treatment duration, treatment current levels, etc. to microcontroller 112 by way of input device 120.

The programmable nature of microcontroller 112 allows for advanced functionality not present in other oral electrical treatment devices. For example, the software on microcontroller 112 could be programmed to run a predetermined treatment regimen. This treatment regimen could include but not be limited to such factors as: treatment duration, treatment current levels, treatment time-of-day, treatment reminders, etc. This treatment regimen could also be programmed by a dental professional by way of input device 120 so that a patient's treatment may be simplified and guaranteed to follow set parameters.

Cathodic electrodes 140 are connected to the positive pole of power source 116 and anodic electrodes 150 are connected to the negative pole of power source 116. These electrodes are placed on the gumline, mounted transversely from one another. This allows a current flow from cathodic electrodes 140 to the gingival tissues, surrounding teeth, boney structures, and connected mouth tissues to anodic electrodes 150 mounted on the transverse gumline and then back to power supply 110, forming a complete circuit.

Power source 116 may be any known device capable of delivering an adjustable direct electrical current. This includes, but is not limited to disposable batteries, rechargeable batteries, AC-DC power converter, etc. Microcontroller 112 is able to regulate the current output of power source 116 by a known method of electrical current control. Power supply 116 is capable of delivering a direct current of between 1 and 500 microamperes, with an approximate range of 50 to 250 microamperes used for most treatments. Microcontroller 112 is also able to reverse the polarity of the cathodic electrodes 140 and anodic electrodes 150 by controlling the output of power source 116. This allows for dynamic changing of electrode polarity during treatment.

Figure 2:
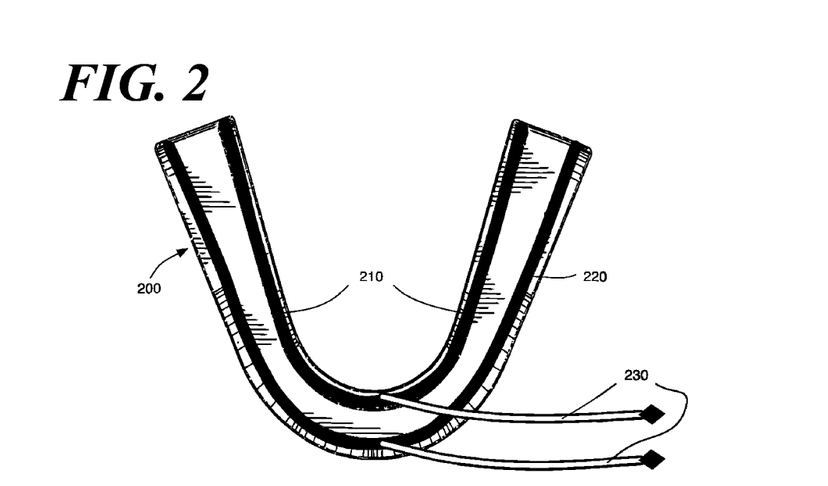
FIG. 2 shows a top-down view of another embodiment that includes a mouthpiece with two continuous electrodes and associated conductors.

FIG. 2 shows a top-down view of another embodiment of the treatment apparatus. In this embodiment, a mouthpiece unit 200, known in the art, has two electrodes attached to or embedded in it, and is worn in the mouth. A single interior gumline electrode 210 fits snugly against the inner gingival tissue of the mouth. A single exterior gumline electrode 220 is attached to or embedded in mouthpiece 200 so that it is transverse from the interior gumline electrode 210 and fits snugly against the outer gingival tissues of the mouth. Two electrical conductors 230 connect electrodes 210 and 220 to an adjustable current power supply, of whose embodiment may be similar to that of 110 or that of FIG. 3. Electrical conductors 230 are insulated so that a short circuit does not occur inside or outside of the mouth. Electrical conductors 230 are shown as attached to the anterior of mouthpiece 200, but may be electrically connected to electrodes 210 and 220 at any point along mouthpiece 200, so long as electrical conductors 230 are not attached to the same electrode.

Figure 3:
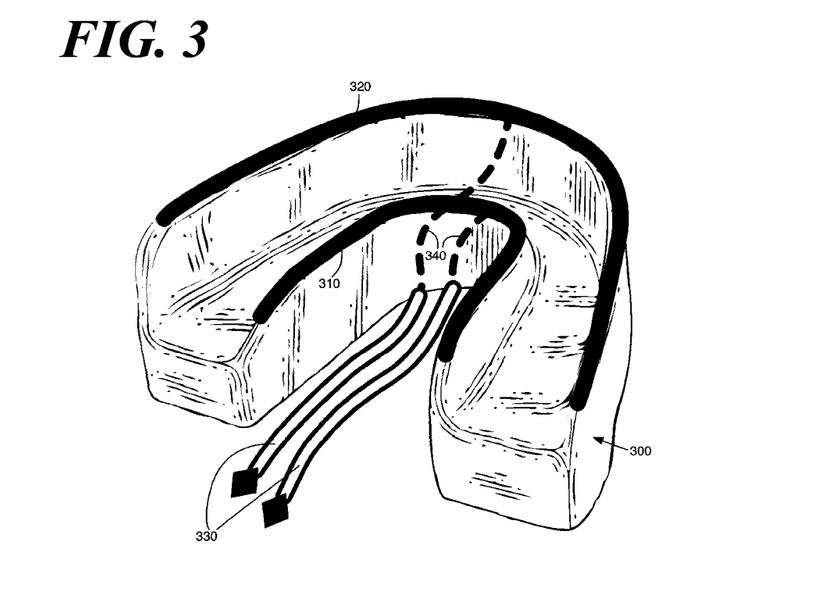
FIG. 3 shows a perspective view of the same embodiment of FIG. 2, with two electrodes embedded in a mouthpiece.

FIG. 3 shows a perspective view of the same type of embodiment shown in FIG. 2. A mouthpiece 300 has an interior gumline electrode 310 and an exterior gumline electrode 320 attached to or embedded it. Electrodes 310 and 320 span the inner and outer gingival surfaces of the mouth, respectively. A set of embedded electrical conductors 340 are connected to electrodes 310 and 320 on one end and on the other end to a set of conductors to the power supply 330. Conductors 340 are embedded in the mouthpiece material and are electrically insulated. Conductors 330 then connect to the positive and negative poles of a direct current power source, similar to that of 110 or FIG. 6.

Figure 4:
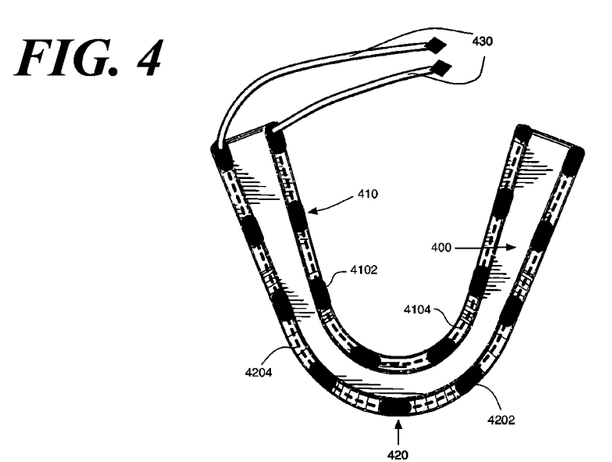
FIG. 4 offers a top-down view of another embodiment similar to FIG. 2 that includes a mouthpiece, but with a plurality of discrete electrodes.

FIG. 4 presents another embodiment similar in nature to that of FIGS. 2 and 3. In this embodiment, electrode sets are attached to or embedded in a mouthpiece unit 400. A set of interior gumline electrodes 410 are affixed to or embedded in mouthpiece 400. Electrode set 410 comprises a plurality of discrete interior gumline electrodes 4102, which are electrically connected by embedded electrical conductors 4104. Conductors 4104 are insulated and are embedded in or attached to mouthpiece 400. Likewise, a set of exterior gumline electrodes 420 are affixed to or embedded in mouthpiece 400 transverse of electrode set 410. Electrode set 420 comprises a plurality of discrete interior gumline electrodes 4202, which are electrically connected by embedded electrical conductors 4204. Conductors 4204 are insulated and are embedded in or attached to mouthpiece 400. This embodiment allows for multiple, discrete points of electrical contact within the mouth. In FIG. 4, conductors to the power supply 430 are shown as attached to the posterior electrodes in mouthpiece 400. However, conductors 430 may be electrically connected to any point of electrode sets 410 and 420, so long as conductors 430 are not connected to the same electrode set. Conductors 430 then connect to the positive and negative poles of a direct current power source, similar to that of 110 or FIG. 6.

Figure 5:
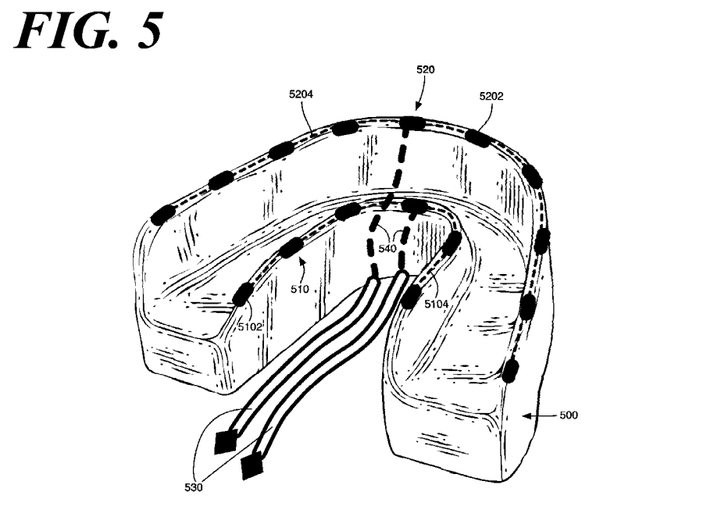
FIG. 5 provides a perspective view of an additional embodiment similar to FIG. 4 with a plurality of electrodes that are electrically connected by embedded conductors.

FIG. 5 offers a perspective view of an embodiment similar to FIG. 4. An interior gumline electrode set 510 and an exterior gumline electrode set 520 are attached to or embedded in a mouthpiece 500. Electrode set 510 comprises a plurality of interior gumline electrodes 5102 that are electrically connected by embedded electrical conductors 5104. Conductors 5104 are electrically insulated and are embedded in or attached to mouthpiece 500. Similarly, electrode set 520 comprises a plurality of exterior gumline electrodes 5202 that are electrically connected by embedded electrical conductors 5204. Conductors 5204 are electrically insulated and are embedded in or attached to mouthpiece 500. Electrode set 520 is mounted transverse of electrode set 510 to allow direct current to flow across the tissue of the teeth and gums. Electrode sets 510 and 520 are connected to conductors to the power supply 530 by way of embedded electrical conductors 540. Conductors 540 are electrically-insulated and are embedded in mouthpiece 500. Conductors 530 then connect to the positive and negative poles of a direct current power source, similar to that of 110 or FIG. 6.

Figure 6:
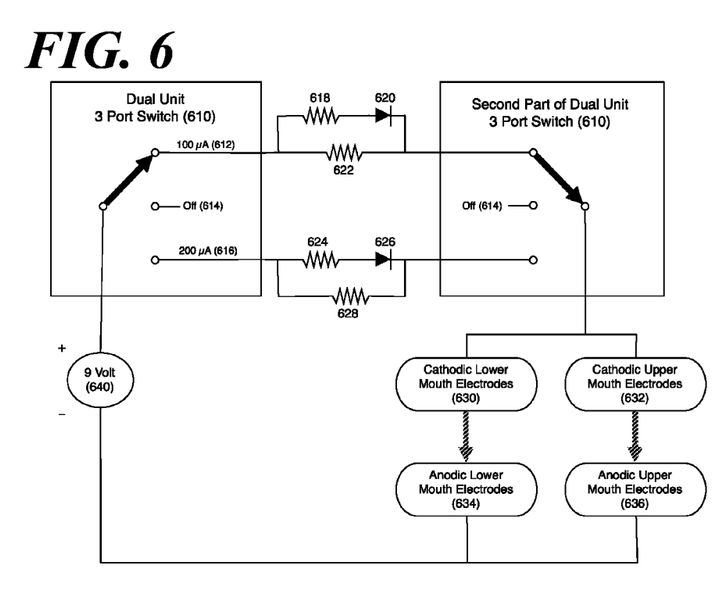
FIG. 6 shows an additional embodiment of with an analog power supply using a dual unit, three-port switch.

FIG. 6 presents another embodiment of an adjustable direct current power source used to supply direct current to a plurality of oral electrodes. This particular circuit design is capable of delivering a steady current regardless of moderate fluctuations in the resistance between the electrodes. The circuit uses a 9-volt power supply 640, which could be a disposable battery, a rechargeable battery, an AC-to-DC converter, or any other suitable 9-volt power source. A dual unit, three-port switch 610 is used to select the current level in the circuit. The three options of the switch circuit are power off 614, 100 µA 612, or 200 µA 616. Switch option 614 simply does not complete a circuit, preventing current from flowing. Switch option 612 comprises a 332 kΩ resistor 618 in series with a 2 volt LED 620. These two components are in parallel with a 48.7 kΩ resistor 622 to provide a 100 microamp current. The Switch option 616 comprises a 665 kΩ resistor 624 in series with a 2 volt LED 626. These two components are in parallel with a 97.6 kΩ resistor 628 to provide a 200 microamp current. Cathodic upper mouth electrodes 630 and cathodic lower mouth electrodes 632 are in parallel with each other and are electrically connected to the output of switch 610. Electrical current then travels from power supply 640 to these electrodes, through the gingival tissues of the mouth to anodic upper mouth electrodes 636 and anodic lower mouth electrodes 634 and finally back to power supply 640. This circuit design will allow moderate and reasonable fluctuations in the resistance across the electrodes and prevent over driving the circuit should the resistance in the mouth vary.

In another embodiment of this invention or in combination with those previously described, an ionic or colloidal medium in the form of a liquid or a gel may be used to decrease electrical resistance in the mouth and to facilitate a more even current distribution across oral electrodes. Any combination of one or more ionic or colloidal compounds may be used. Examples of such a medium would include, but not be limited to, colloidal silver gel, liquid colloidal silver, colloidal copper gel, liquid colloidal copper, colloidal gold gel, liquid colloidal gold, saline gel, liquid saline or any combination thereof. Artificial or natural flavorings may be added to this medium to offer a more appealing taste to the user. The medium may also contain dietary supplements including, but not limited to, oil of oregano. This medium may also contain teeth-whitening chemical agents. A whitening agent that is catalyzed by the direct current would be most effective in this ionic or colloidal medium.

In yet another embodiment, microcontrolled power supply 110 would be miniaturized and be physically attached to a mouthpiece similar to 200, 300, 400, or 500. This would allow for an all-in-one unit that would fit inside the user's mouth. In this embodiment, power source 116 would have to be of small physical size. One of many possible options is a watch-type battery or other small, portable power source. This circuitry would then be encased in a waterproof manner in the material of the mouthpiece itself. Input device 120 and feedback device 130 would be waterproofed and protected from any kind of electrical shorting, as well.

Thus the reader will see that at least one embodiment addresses a desired need in the oral hygiene and dental fields to concurrently treat common oral diseases and conditions in a more effective, less invasive, and less expensive manner. These embodiments promote general oral hygiene, treat periodontal diseases such as gingivitis and perdiodontitis, kill oral microbes including bacteria and thus preventing cavities and tooth decay, increase vasodilation and blood flow in oral tissues, promote gingival tissue regeneration, foster osteogenesis in the boney structures of the teeth, mouth, and related areas, and treat other periodontal and oral maladies through the non-invasive application of weak direct current electricity to the surfaces in the oral cavity.

While our above descriptions contain many specificities, these should not be construed as limitations on the invention, but rather as an exemplification of several preferred embodiments thereof. Many other variations are possible. For example, electrodes may be attached directly to the gumline without the use of a mouthpiece, perhaps using an electrically-conductive paste. Or electrodes may be placed in contact with tissues neighboring the gumline, such as the teeth or tissues of the cheek, instead of directly on the gumline to accomplish the same result. Another example would be replacing LEDs 626 and 620 from FIG. 6 with standard diodes to achieve the same resultant circuit. Overall, the circuitry from FIGS. 1 and 6 could be altered in many ways to deliver the same electrical current to the oral electrodes.

Accordingly, the scope of the invention should be determined not by the embodiments illustrated, but by the appended claims and their legal equivalents.

We claim:

1. A method for promoting oral hygiene, the method comprising the steps of:
    (a) providing a mouthpiece supporting a plurality of electrodes coupled to a variable direct current power source;
    (b) positioning a first electrode of said plurality of electrodes between a cheek and an exterior gumline of a human, and in physical contact with gingival tissue;
    (c) positioning a second electrode of said plurality of electrodes medial to said first electrode, and in physical contact with gingival tissue;
    (d) delivering direct current from said power source to said gingival tissue,
    (e) regulating said current delivered to said gingival tissues to approximately between 1 and 500 microamperes; and
    (f) wherein said first electrode and said second electrode maintain opposing polarity such that said direct current is delivered from one of said first or said second electrodes to said gingival tissue and surrounding oral structures, to the other of said first or said second electrodes on a transverse gumline.

2. The method of claim 1, further including the step of applying an electrically-conductive medium to said gingival tissue.

3. The method of claim 2, wherein said electrically-conductive medium comprises a teeth whitening agent.

4. The method of claim 2, further including flavoring substances added to said electrically-conductive medium.

5. The method of claim 2, further including oil of oregano added to said electrically-conductive medium.

6. The method of claim 1, further comprising at least one of the steps in the group consisting of: killing oral microbes, increasing oral circulation, fostering gingival regeneration, and promoting osteogenesis.

7. The method of claim 1, wherein the first electrode and second electrode are exposed electrodes supported by a mouthpiece, said mouthpiece comprising an arcuate trough, wherein said first electrode is disposed on a first side of said trough and said second electrode is disposed on a second side of said trough.

8. The method of claim 1, wherein said regulating step comprises a step of regulating said current delivered to said gingival tissues to approximately between 50 and 250 microamperes.

9. The method of claim 1, wherein said exterior gumline is disposed at least one of lateral and anterior to a portion of a mandible of said human.

10. The method of claim 9, wherein said interior gumline is disposed at least one of medial and posterior to said portion of said mandible.

11. The method of claim 1, wherein said first electrode and said second electrode comprise the same electrode material.

12. The method of claim 11, wherein said electrode material is selected from the group consisting of silver, stainless steel, copper, gold, platinum, palladium, aluminum, aluminum alloy, electrically-conductive nanotubes, carbonized rubber, electrically-conductive silicone, and electrically conductive polymer.

13. An apparatus for promoting oral hygiene, said apparatus comprising:
    (a) a variable direct current power source capable of delivering approximately 1 to 500 microamperes,
    (b) a plurality of exposed electrodes coupled to said direct current power source, and
    (c) a mouthpiece comprising an arcuate trough, wherein a first of said exposed electrodes is a cathode electrode disposed on a first side of said trough and a second of said exposed electrodes is an anode electrode disposed on a second side of said trough, wherein when the mouthpiece is inserted into a mouth of a human, each of said exposed electrodes physically contacts gingival tissue of said human.

14. The apparatus of claim 13 wherein said exposed electrodes are partially embedded in said mouthpiece.

15. The apparatus of claim 14 wherein said power source is embedded in said mouthpiece.

* * * * *

UNITED STATES PATENT AND TRADEMARK OFFICE
CERTIFICATE OF CORRECTION

PATENT NO. : 8,660,669 B2
APPLICATION NO. : 12/205062
DATED : February 25, 2014
INVENTOR(S) : Nemeh et al.

It is certified that error appears in the above-identified patent and that said Letters Patent is hereby corrected as shown below:

On the title page

Item (56) Reference Cited Other Publications, page 2, column 1, line 16, under "Dei Pozo, J.L. et al., Effect of Electrical Current..." delete "Dei Pozo, J.L." and substitute -- Del Pozo, J.L. --

Item (56) Reference Cited Other Publications, page 2, column 1, line 19, under "Del Pozo, J.L." delete "Eiectricidal" and substitute -- Electricidal --

Item (56) Reference Cited Other Publications, page 2, column 1, under "Buch, F." delete "Biomateriais" and substitute -- Biomaterials --

Item (56) Reference Cited Other Publications, page 2, column 2, line 13, under "Sandhi, SP., et al.," delete "Sandhi, SP., et al.," and substitute -- Sandhu, SP., et al., --

Item (56) Reference Cited Other Publications, page 2, column 2, line 22, under "Chakkalakai, DA., et al., " delete "Chakkalakai, DA., et al.," and substitute -- Chakkalakal, DA., et al., --

Signed and Sealed this
First Day of July, 2014

Michelle K. Lee
*Deputy Director of the United States Patent and Trademark Office*